(12) United States Patent
Li et al.

(10) Patent No.: US 9,133,516 B2
(45) Date of Patent: Sep. 15, 2015

(54) METHODS FOR IDENTIFICATION OF ALLELES USING ALLELE-SPECIFIC PRIMERS FOR AMPLIFICATION

(75) Inventors: Caixia Li, Beijing (CN); Huafang Gao, Beijing (CN); Xiang Liu, Beijing (CN); Bin Cai, Beijing (CN); Di Zhang, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 1373 days.

(21) Appl. No.: 12/305,193

(22) PCT Filed: Jun. 29, 2007

(86) PCT No.: PCT/CN2007/002039
§ 371 (c)(1),
(2), (4) Date: Jul. 6, 2009

(87) PCT Pub. No.: WO2008/003244
PCT Pub. Date: Jan. 10, 2008

(65) Prior Publication Data
US 2010/0041563 A1 Feb. 18, 2010

(30) Foreign Application Priority Data

Jun. 30, 2006 (CN) .......................... 2006 1 0089526

(51) Int. Cl.
*C12Q 1/68* (2006.01)

(52) U.S. Cl.
CPC ............ *C12Q 1/6883* (2013.01); *C12Q 1/6858* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,475,610 A * | 12/1995 | Atwood et al. | 700/269 |
| 5,780,233 A | 7/1998 | Guo et al. | |
| 6,506,594 B1 | 1/2003 | Barany et al. | |
| 6,709,816 B1 * | 3/2004 | Huang et al. | 435/6.12 |
| 2010/0151448 A1 * | 6/2010 | Zhang et al. | 435/6 |

FOREIGN PATENT DOCUMENTS

| | | |
|---|---|---|
| WO | WO-99/29901 | 6/1999 |
| WO | WO 0047766 A1 * | 8/2000 |
| WO | WO-01/29259 | 4/2001 |
| WO | WO-2005/047533 | 5/2005 |
| WO | WO-2006/021131 | 3/2006 |

OTHER PUBLICATIONS

Engle et al., Using high-throughput SNP technologieis to study cancer, Oncogene, Mar. 2006, vol. 25, pp. 1594-1601.*
Shen et al., High-throughput SNP genotyping on universal bead arrays, Mutation Research 573 (2005) 70-82.*
Duman et al., Mitochondrial DNA alterations involving position 961 are not sufficient to explain sensorineural hearing loss, The Mediterranean Society of Otology and Audiology, Mediterr J Otol 2005; 1:110-116.*
Brownie et al. Nucleic Acids Research (1997) 25(16): 3235-3241.*
Hamelmann et al. Human Mutation, Mutation in Brief #428 (2001) Online, 6 pages.*
Tsukamoto et al. European Journal of Human Genetics (2003) 11: 916-922.*
Xia et al. Nature Genetics (1998) 20: 370-373.*
Estivill et al. American Journal of Human Genetics (1998) 62(1): 27-35.*
Boniotto et al., J. Immunol. Methods (2005) 304:184-188.
Eaker et al., Biosensors Bioelectronics (2005) 21:933-939.
Ferrie et al., Am. J. Hum. Genet. (1992) 51:251-262.
Gomez-Llorente et al., Early Hum. Dev. (2001) 65:S161-S164.
International Search Report for PCT/CN2007/002039, mailed on Sep. 6, 2007, 2 pages.
Newton et al., Nucleic Acid Res. (1989) 17:2503-2516.
Written Opinion of the International Searching Authority for PCT/CN2007/002039, mailed on Sep. 6, 2007, 3 pages.

* cited by examiner

*Primary Examiner* — Angela M Bertagna
(74) *Attorney, Agent, or Firm* — Morrison & Foerster LLP

(57) ABSTRACT

The invention provides a method for identification of alleles. In this method, genomic DNA is used as target. Multiple allele-specific PCR amplification are carried out with a group of primers comprising one or more allele-specific primers for a target gene, a universal primer, and a common primer; and a DNA polymerase without 5' to 3' exonuclease activity. The PCR products are hybridized with tag probes immobilized on a DNA chip. Results are determined based on the signal intensity and the position of the probe immobilized on the array. Each allele-specific primer comprises a unique tag sequence at the 5' end. Each tag probe immobilized on the DNA chip comprises a sequence identical to its corresponding tag sequence; and each tag probe hybridizes only with the complementary sequence in the PCR amplification product.

10 Claims, 4 Drawing Sheets

SEQUENCE LISTING

<160> NUMBER OF SEQ ID NOS: 77

<210> SEQ ID NO 1
<211> LENGTH: 22
<212> TYPE: DNA
<213> ORGANISM: Artificial Sequence
<220> FEATURE:
<223> OTHER INFORMATION: synthetic construct

<400> SEQUENCE: 1
gttactgcta cgcgtgctac gt                                              22

<210> SEQ ID NO 2
<211> LENGTH: 22
<212> TYPE: DNA
<213> ORGANISM: Artificial Sequence
<220> FEATURE:
<223> OTHER INFORMATION: synthetic construct

<400> SEQUENCE: 2
catgagcaag ctgtctaagg cg                                              22

<210> SEQ ID NO 3
<211> LENGTH: 21
<212> TYPE: DNA
<213> ORGANISM: Artificial Sequence
<220> FEATURE:
<223> OTHER INFORMATION: synthetic construct

<400> SEQUENCE: 3
cgacgagctg ccgcgcaaga t                                               21

<210> SEQ ID NO 4
<211> LENGTH: 21
<212> TYPE: DNA
<213> ORGANISM: Artificial Sequence
<220> FEATURE:
<223> OTHER INFORMATION: synthetic construct

<400> SEQUENCE: 4
tatcgcgacc gcatccaatc t                                               21

<210> SEQ ID NO 5
<211> LENGTH: 21
<212> TYPE: DNA
<213> ORGANISM: Artificial Sequence
<220> FEATURE:
<223> OTHER INFORMATION: synthetic construct

<400> SEQUENCE: 5
gctcgaagag ggctacagat c                                               21

<210> SEQ ID NO 6
<211> LENGTH: 22
<212> TYPE: DNA
<213> ORGANISM: Artificial Sequence
<220> FEATURE:
<223> OTHER INFORMATION: synthetic construct

<400> SEQUENCE: 6
ttcccgtccg tcatcgctca ag                                              22

<210> SEQ ID NO 7
<211> LENGTH: 21
<212> TYPE: DNA
<213> ORGANISM: Artificial Sequence

```
<220> FEATURE:
<223> OTHER INFORMATION: synthetic construct

<400> SEQUENCE: 7
gatcggcggt gaagcgaaag g                                              21

<210> SEQ ID NO 8
<211> LENGTH: 21
<212> TYPE: DNA
<213> ORGANISM: Artificial Sequence
<220> FEATURE:
<223> OTHER INFORMATION: synthetic construct

<400> SEQUENCE: 8
gatggtgatc tcgcgcgtgc g                                              21

<210> SEQ ID NO 9
<211> LENGTH: 21
<212> TYPE: DNA
<213> ORGANISM: Artificial Sequence
<220> FEATURE:
<223> OTHER INFORMATION: synthetic construct

<400> SEQUENCE: 9
tgtgcgcccg agttcggtat c                                              21

<210> SEQ ID NO 10
<211> LENGTH: 22
<212> TYPE: DNA
<213> ORGANISM: Artificial Sequence
<220> FEATURE:
<223> OTHER INFORMATION: synthetic construct

<400> SEQUENCE: 10
ttgatcccat cgaaggacga tg                                             22

<210> SEQ ID NO 11
<211> LENGTH: 22
<212> TYPE: DNA
<213> ORGANISM: Artificial Sequence
<220> FEATURE:
<223> OTHER INFORMATION: synthetic construct

<400> SEQUENCE: 11
tgatgcgtct gggacgtgcc tg                                             22

<210> SEQ ID NO 12
<211> LENGTH: 21
<212> TYPE: DNA
<213> ORGANISM: Artificial Sequence
<220> FEATURE:
<223> OTHER INFORMATION: synthetic construct

<400> SEQUENCE: 12
cagagcatca acgacgcagg a                                              21

<210> SEQ ID NO 13
<211> LENGTH: 21
<212> TYPE: DNA
<213> ORGANISM: Artificial Sequence
<220> FEATURE:
<223> OTHER INFORMATION: synthetic construct

<400> SEQUENCE: 13
acgatcaacg cggagacaca g                                              21
```

<210> SEQ ID NO 14
<211> LENGTH: 21
<212> TYPE: DNA
<213> ORGANISM: Artificial Sequence
<220> FEATURE:
<223> OTHER INFORMATION: synthetic construct

<400> SEQUENCE: 14
acgagacacg caacgagaca g                                              21

<210> SEQ ID NO 15
<211> LENGTH: 21
<212> TYPE: DNA
<213> ORGANISM: Artificial Sequence
<220> FEATURE:
<223> OTHER INFORMATION: synthetic construct

<400> SEQUENCE: 15
ttgaaagcct acacgcgagc g                                              21

<210> SEQ ID NO 16
<211> LENGTH: 22
<212> TYPE: DNA
<213> ORGANISM: Artificial Sequence
<220> FEATURE:
<223> OTHER INFORMATION: synthetic construct

<400> SEQUENCE: 16
caagcagagc tatggttcgc tg                                             22

<210> SEQ ID NO 17
<211> LENGTH: 22
<212> TYPE: DNA
<213> ORGANISM: Artificial Sequence
<220> FEATURE:
<223> OTHER INFORMATION: synthetic construct

<400> SEQUENCE: 17
gtcagtatcg cgttcgctta cg                                             22

<210> SEQ ID NO 18
<211> LENGTH: 21
<212> TYPE: DNA
<213> ORGANISM: Artificial Sequence
<220> FEATURE:
<223> OTHER INFORMATION: synthetic construct

<400> SEQUENCE: 18
ccatactcac gcaactgtgc a                                              21

<210> SEQ ID NO 19
<211> LENGTH: 22
<212> TYPE: DNA
<213> ORGANISM: Artificial Sequence
<220> FEATURE:
<223> OTHER INFORMATION: synthetic construct

<400> SEQUENCE: 19
gttagggtcg gccaaactct cc                                             22

<210> SEQ ID NO 20
<211> LENGTH: 22
<212> TYPE: DNA
<213> ORGANISM: Artificial Sequence
<220> FEATURE:
<223> OTHER INFORMATION: synthetic construct

<400> SEQUENCE: 20
gacaaaggtc tgcccagcac ca                                                    22

<210> SEQ ID NO 21
<211> LENGTH: 22
<212> TYPE: DNA
<213> ORGANISM: Artificial Sequence
<220> FEATURE:
<223> OTHER INFORMATION: synthetic construct

<400> SEQUENCE: 21
tgcaacacgc taggatctcc tc                                                    22

<210> SEQ ID NO 22
<211> LENGTH: 22
<212> TYPE: DNA
<213> ORGANISM: Artificial Sequence
<220> FEATURE:
<223> OTHER INFORMATION: synthetic construct

<400> SEQUENCE: 22
tgcacttctc ggtaggcagc ga                                                    22

<210> SEQ ID NO 23
<211> LENGTH: 42
<212> TYPE: DNA
<213> ORGANISM: Artificial Sequence
<220> FEATURE:
<223> OTHER INFORMATION: synthetic construct

<400> SEQUENCE: 23
gttactgcta cgcgtgctac gttgtttgtt cacacccgc ag                               42

<210> SEQ ID NO 24
<211> LENGTH: 41
<212> TYPE: DNA
<213> ORGANISM: Artificial Sequence
<220> FEATURE:
<223> OTHER INFORMATION: synthetic construct

<400> SEQUENCE: 24
catgagcaag ctgtctaagg cgtgtttgtt cacacccgca g                               41

<210> SEQ ID NO 25
<211> LENGTH: 39
<212> TYPE: DNA
<213> ORGANISM: Artificial Sequence
<220> FEATURE:
<223> OTHER INFORMATION: synthetic construct

<400> SEQUENCE: 25
gcacgctatc acgttagacg catgcttgct tacccagac                                  39

<210> SEQ ID NO 26
<211> LENGTH: 43
<212> TYPE: DNA
<213> ORGANISM: Artificial Sequence
<220> FEATURE:
<223> OTHER INFORMATION: synthetic construct

<400> SEQUENCE: 26
cgacgagctg ccgcgcaaga tcgactttgt ctgcaacacc ctg                             43

<210> SEQ ID NO 27

<210> SEQ ID NO 27
<211> LENGTH: 40
<212> TYPE: DNA
<213> ORGANISM: Artificial Sequence
<220> FEATURE:
<223> OTHER INFORMATION: synthetic construct

<400> SEQUENCE: 27
tatcgcgacc gcatccaatc tactttgtct gcaacacccg                    40

<210> SEQ ID NO 28
<211> LENGTH: 41
<212> TYPE: DNA
<213> ORGANISM: Artificial Sequence
<220> FEATURE:
<223> OTHER INFORMATION: synthetic construct

<400> SEQUENCE: 28
gctcgaagag ggctacagat cccaggctgc aagaacgtgt g                  41

<210> SEQ ID NO 29
<211> LENGTH: 40
<212> TYPE: DNA
<213> ORGANISM: Artificial Sequence
<220> FEATURE:
<223> OTHER INFORMATION: synthetic construct

<400> SEQUENCE: 29
ttcccgtccg tcatcgctca agaccctgca gccagctacg                    40

<210> SEQ ID NO 30
<211> LENGTH: 39
<212> TYPE: DNA
<213> ORGANISM: Artificial Sequence
<220> FEATURE:
<223> OTHER INFORMATION: synthetic construct

<400> SEQUENCE: 30
gatcggcggt gaagcgaaag gatccggcta tgggccctg                     39

<210> SEQ ID NO 31
<211> LENGTH: 38
<212> TYPE: DNA
<213> ORGANISM: Artificial Sequence
<220> FEATURE:
<223> OTHER INFORMATION: synthetic construct

<400> SEQUENCE: 31
gatggtgatc tcgcgcgtgc gatccggcta tgggcctg                      38

<210> SEQ ID NO 32
<211> LENGTH: 40
<212> TYPE: DNA
<213> ORGANISM: Artificial Sequence
<220> FEATURE:
<223> OTHER INFORMATION: synthetic construct

<400> SEQUENCE: 32
tgtgcgcccg agttcggtat ctggcctacc ggagacatga                    40

<210> SEQ ID NO 33
<211> LENGTH: 41
<212> TYPE: DNA
<213> ORGANISM: Artificial Sequence
<220> FEATURE:
<223> OTHER INFORMATION: synthetic construct

<400> SEQUENCE: 33
ttgatcccat cgaaggacga tgcgtggcct accggagacg a         41

<210> SEQ ID NO 34
<211> LENGTH: 37
<212> TYPE: DNA
<213> ORGANISM: Artificial Sequence
<220> FEATURE:
<223> OTHER INFORMATION: synthetic construct

<400> SEQUENCE: 34
gcacgctatc acgttagacg agccttcgat gcggacc              37

<210> SEQ ID NO 35
<211> LENGTH: 41
<212> TYPE: DNA
<213> ORGANISM: Artificial Sequence
<220> FEATURE:
<223> OTHER INFORMATION: synthetic construct

<400> SEQUENCE: 35
tgatgcgtct gggacgtgcc tggtggactg ctacattggc c         41

<210> SEQ ID NO 36
<211> LENGTH: 40
<212> TYPE: DNA
<213> ORGANISM: Artificial Sequence
<220> FEATURE:
<223> OTHER INFORMATION: synthetic construct

<400> SEQUENCE: 36
cagagcatca acgacgcagg agtggactgc tacattggct           40

<210> SEQ ID NO 37
<211> LENGTH: 39
<212> TYPE: DNA
<213> ORGANISM: Artificial Sequence
<220> FEATURE:
<223> OTHER INFORMATION: synthetic construct

<400> SEQUENCE: 37
acgatcaacg cggagacaca gacattgcca gacctaccg            39

<210> SEQ ID NO 38
<211> LENGTH: 40
<212> TYPE: DNA
<213> ORGANISM: Artificial Sequence
<220> FEATURE:
<223> OTHER INFORMATION: synthetic construct

<400> SEQUENCE: 38
acgagacacg caacgagaca gtacattgcc agacctacca           40

<210> SEQ ID NO 39
<211> LENGTH: 38
<212> TYPE: DNA
<213> ORGANISM: Artificial Sequence
<220> FEATURE:
<223> OTHER INFORMATION: synthetic construct

<400> SEQUENCE: 39
gcacgctatc acgttagact cgaggcttgt ccttgtgc             38

<210> SEQ ID NO 40
<211> LENGTH: 41
<212> TYPE: DNA

<213> ORGANISM: Artificial Sequence
<220> FEATURE:
<223> OTHER INFORMATION: synthetic construct

<400> SEQUENCE: 40
ttgaaagcct acacgcgagc gcaagtgctg gtctcacagc t                    41

<210> SEQ ID NO 41
<211> LENGTH: 41
<212> TYPE: DNA
<213> ORGANISM: Artificial Sequence
<220> FEATURE:
<223> OTHER INFORMATION: synthetic construct

<400> SEQUENCE: 41
caagcagagc tatggttcgc tgaagtgctg gtctcacagc c                    41

<210> SEQ ID NO 42
<211> LENGTH: 41
<212> TYPE: DNA
<213> ORGANISM: Artificial Sequence
<220> FEATURE:
<223> OTHER INFORMATION: synthetic construct

<400> SEQUENCE: 42
gcacgctatc acgttagacg aggtctcacg tctcaaactc c                    41

<210> SEQ ID NO 43
<211> LENGTH: 45
<212> TYPE: DNA
<213> ORGANISM: Artificial Sequence
<220> FEATURE:
<223> OTHER INFORMATION: synthetic construct

<400> SEQUENCE: 43
gttagggtcg gccaaactct ccgacacatt cttttgtcg gtcca                 45

<210> SEQ ID NO 44
<211> LENGTH: 42
<212> TYPE: DNA
<213> ORGANISM: Artificial Sequence
<220> FEATURE:
<223> OTHER INFORMATION: synthetic construct

<400> SEQUENCE: 44
gacaaaggtc tgcccagcac caacattctt tttgacggtc cg                   42

<210> SEQ ID NO 45
<211> LENGTH: 41
<212> TYPE: DNA
<213> ORGANISM: Artificial Sequence
<220> FEATURE:
<223> OTHER INFORMATION: synthetic construct

<400> SEQUENCE: 45
gcacgctatc acgttagacc aaggttttcc agattgctga g                    41

<210> SEQ ID NO 46
<211> LENGTH: 45
<212> TYPE: DNA
<213> ORGANISM: Artificial Sequence
<220> FEATURE:
<223> OTHER INFORMATION: synthetic construct

<400> SEQUENCE: 46
tgcaacacgc taggatctcc tcaatggcag tagcaattat cgact                45

```
<210> SEQ ID NO 47
<211> LENGTH: 43
<212> TYPE: DNA
<213> ORGANISM: Artificial Sequence
<220> FEATURE:
<223> OTHER INFORMATION: synthetic construct

<400> SEQUENCE: 47
tgcacttctc ggtaggcagc gatggcagta gcaattatcg tcc           43

<210> SEQ ID NO 48
<211> LENGTH: 39
<212> TYPE: DNA
<213> ORGANISM: Artificial Sequence
<220> FEATURE:
<223> OTHER INFORMATION: synthetic construct

<400> SEQUENCE: 48
gcacgctatc acgttagacc gtgtagcagc aggaagtat                39

<210> SEQ ID NO 49
<211> LENGTH: 43
<212> TYPE: DNA
<213> ORGANISM: Artificial Sequence
<220> FEATURE:
<223> OTHER INFORMATION: synthetic construct

<400> SEQUENCE: 49
gtcagtatcg cgttcgctta cgacttacca tgttacgact agt           43

<210> SEQ ID NO 50
<211> LENGTH: 43
<212> TYPE: DNA
<213> ORGANISM: Artificial Sequence
<220> FEATURE:
<223> OTHER INFORMATION: synthetic construct

<400> SEQUENCE: 50
ccatactcac gcaactgtgc acacttacca tgttacgact tgc           43

<210> SEQ ID NO 51
<211> LENGTH: 39
<212> TYPE: DNA
<213> ORGANISM: Artificial Sequence
<220> FEATURE:
<223> OTHER INFORMATION: synthetic construct

<400> SEQUENCE: 51
gcacgctatc acgttagacc cctgatgaag gctacaaag               39

<210> SEQ ID NO 52
<211> LENGTH: 19
<212> TYPE: DNA
<213> ORGANISM: Artificial Sequence
<220> FEATURE:
<223> OTHER INFORMATION: synthetic construct

<400> SEQUENCE: 52
gcacgctatc acgttagac                                      19

<210> SEQ ID NO 53
<211> LENGTH: 35
<212> TYPE: DNA
<213> ORGANISM: Artificial Sequence
<220> FEATURE:
```

```
<223> OTHER INFORMATION: synthetic construct

<400> SEQUENCE: 53
tttttttttt tttttagagt gcttggtgcc ataac                              35

<210> SEQ ID NO 54
<211> LENGTH: 32
<212> TYPE: DNA
<213> ORGANISM: Artificial Sequence
<220> FEATURE:
<223> OTHER INFORMATION: synthetic construct

<400> SEQUENCE: 54
tttttttttt tttttgcaac caccaccgga gg                                 32

<210> SEQ ID NO 55
<211> LENGTH: 39
<212> TYPE: DNA
<213> ORGANISM: Artificial Sequence
<220> FEATURE:
<223> OTHER INFORMATION: synthetic construct

<400> SEQUENCE: 55
tttttttttt tttttggtat cgcgaccgca tcccaatct                          39

<210> SEQ ID NO 56
<211> LENGTH: 37
<212> TYPE: DNA
<213> ORGANISM: Artificial Sequence
<220> FEATURE:
<223> OTHER INFORMATION: synthetic construct

<400> SEQUENCE: 56
tttttttttt tttttgttac tgctacgcgt gctacgt                            37

<210> SEQ ID NO 57
<211> LENGTH: 37
<212> TYPE: DNA
<213> ORGANISM: Artificial Sequence
<220> FEATURE:
<223> OTHER INFORMATION: synthetic construct

<400> SEQUENCE: 57
tttttttttt tttttcatga gcaagctgtc taaggcg                            37

<210> SEQ ID NO 58
<211> LENGTH: 36
<212> TYPE: DNA
<213> ORGANISM: Artificial Sequence
<220> FEATURE:
<223> OTHER INFORMATION: synthetic construct

<400> SEQUENCE: 58
tttttttttt tttttcgacg agctgccgcg caagat                             36

<210> SEQ ID NO 59
<211> LENGTH: 36
<212> TYPE: DNA
<213> ORGANISM: Artificial Sequence
<220> FEATURE:
<223> OTHER INFORMATION: synthetic construct

<400> SEQUENCE: 59
tttttttttt ttttttatcg cgaccgcatc caatct                             36
```

```
<210> SEQ ID NO 60
<211> LENGTH: 36
<212> TYPE: DNA
<213> ORGANISM: Artificial Sequence
<220> FEATURE:
<223> OTHER INFORMATION: synthetic construct

<400> SEQUENCE: 60
tttttttttt tttttgctcg aagagggcta cagatc                               36

<210> SEQ ID NO 61
<211> LENGTH: 37
<212> TYPE: DNA
<213> ORGANISM: Artificial Sequence
<220> FEATURE:
<223> OTHER INFORMATION: synthetic construct

<400> SEQUENCE: 61
tttttttttt tttttttccc gtccgtcatc gctcaag                              37

<210> SEQ ID NO 62
<211> LENGTH: 36
<212> TYPE: DNA
<213> ORGANISM: Artificial Sequence
<220> FEATURE:
<223> OTHER INFORMATION: synthetic construct

<400> SEQUENCE: 62
tttttttttt tttttgatcg gcggtgaagc gaaagg                               36

<210> SEQ ID NO 63
<211> LENGTH: 36
<212> TYPE: DNA
<213> ORGANISM: Artificial Sequence
<220> FEATURE:
<223> OTHER INFORMATION: synthetic construct

<400> SEQUENCE: 63
tttttttttt tttttgatgg tgatctcgcg cgtgcg                               36

<210> SEQ ID NO 64
<211> LENGTH: 36
<212> TYPE: DNA
<213> ORGANISM: Artificial Sequence
<220> FEATURE:
<223> OTHER INFORMATION: synthetic construct

<400> SEQUENCE: 64
tttttttttt tttttgtgc gcccgagttc ggtatc                                36

<210> SEQ ID NO 65
<211> LENGTH: 37
<212> TYPE: DNA
<213> ORGANISM: Artificial Sequence
<220> FEATURE:
<223> OTHER INFORMATION: synthetic construct

<400> SEQUENCE: 65
tttttttttt tttttttgat cccatcgaag gacgatg                              37

<210> SEQ ID NO 66
<211> LENGTH: 37
<212> TYPE: DNA
<213> ORGANISM: Artificial Sequence
<220> FEATURE:
<223> OTHER INFORMATION: synthetic construct
```

<400> SEQUENCE: 66
tttttttttt tttttttgatg cgtctgggac gtgcctg          37

<210> SEQ ID NO 67
<211> LENGTH: 36
<212> TYPE: DNA
<213> ORGANISM: Artificial Sequence
<220> FEATURE:
<223> OTHER INFORMATION: synthetic construct

<400> SEQUENCE: 67
tttttttttt tttttcagag catcaacgac gcagga          36

<210> SEQ ID NO 68
<211> LENGTH: 36
<212> TYPE: DNA
<213> ORGANISM: Artificial Sequence
<220> FEATURE:
<223> OTHER INFORMATION: synthetic construct

<400> SEQUENCE: 68
tttttttttt tttttacgat caacgcggag acacag          36

<210> SEQ ID NO 69
<211> LENGTH: 36
<212> TYPE: DNA
<213> ORGANISM: Artificial Sequence
<220> FEATURE:
<223> OTHER INFORMATION: synthetic construct

<400> SEQUENCE: 69
tttttttttt tttttacgag acacgcaacg agacag          36

<210> SEQ ID NO 70
<211> LENGTH: 36
<212> TYPE: DNA
<213> ORGANISM: Artificial Sequence
<220> FEATURE:
<223> OTHER INFORMATION: synthetic construct

<400> SEQUENCE: 70
tttttttttt tttttttgaa agcctacacg cgagcg          36

<210> SEQ ID NO 71
<211> LENGTH: 37
<212> TYPE: DNA
<213> ORGANISM: Artificial Sequence
<220> FEATURE:
<223> OTHER INFORMATION: synthetic construct

<400> SEQUENCE: 71
tttttttttt tttttcaagc agagctatgg ttcgctg          37

<210> SEQ ID NO 72
<211> LENGTH: 37
<212> TYPE: DNA
<213> ORGANISM: Artificial Sequence
<220> FEATURE:
<223> OTHER INFORMATION: synthetic construct

<400> SEQUENCE: 72
tttttttttt tttttgtcag tatcgcgttc gcttacg          37

<210> SEQ ID NO 73
<211> LENGTH: 36

```
<212> TYPE: DNA
<213> ORGANISM: Artificial Sequence
<220> FEATURE:
<223> OTHER INFORMATION: synthetic construct

<400> SEQUENCE: 73
tttttttttt tttttccata ctcacgcaac tgtgca                              36

<210> SEQ ID NO 74
<211> LENGTH: 37
<212> TYPE: DNA
<213> ORGANISM: Artificial Sequence
<220> FEATURE:
<223> OTHER INFORMATION: synthetic construct

<400> SEQUENCE: 74
tttttttttt tttttgttag ggtcggccaa actctcc                             37

<210> SEQ ID NO 75
<211> LENGTH: 37
<212> TYPE: DNA
<213> ORGANISM: Artificial Sequence
<220> FEATURE:
<223> OTHER INFORMATION: synthetic construct

<400> SEQUENCE: 75
tttttttttt tttttgacaa aggtctgccc agcacca                             37

<210> SEQ ID NO 76
<211> LENGTH: 37
<212> TYPE: DNA
<213> ORGANISM: Artificial Sequence
<220> FEATURE:
<223> OTHER INFORMATION: synthetic construct

<400> SEQUENCE: 76
tttttttttt ttttttgcaa cacgctagga tctcctc                             37

<210> SEQ ID NO 77
<211> LENGTH: 37
<212> TYPE: DNA
<213> ORGANISM: Artificial Sequence
<220> FEATURE:
<223> OTHER INFORMATION: synthetic construct

<400> SEQUENCE: 77
tttttttttt ttttttgcac ttctcggtag gcagcga                             37
```

METHODS FOR IDENTIFICATION OF ALLELES USING ALLELE-SPECIFIC PRIMERS FOR AMPLIFICATION

CROSS-REFERENCE TO RELATED APPLICATIONS

This application is the national phase of PCT application PCT/CN2007/002039 having an international filing date of Jun 29, 2007, which claims priority from China application number 200610089526.7 filed Jun. 30, 2006. The contents of these documents are incorporated herein by this reference.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 514572004600Seqlist.txt | Dec. 14, 2011 | 14,180 bytes |

FIELD OF THE INVENTION

The present invention is related to methods of identification of alleles in gene analysis field.

BACKGROUND OF THE INVENTION

Because genetic polymorphism analysis has important application values in the fields of biomedical research and clinical practice, various techniques have been established to determine genetic polymorphisms. Some of the classical techniques include Restriction Fragment Length Polymorphism (RFLP), Single Strand Conformation Polymorphism (SSCP), Sequence Based Typing (SBT), Denaturing High Performance Liquid Chromatography (DHPLC), Allele-Specific PCR (ASPCR), Sequence Specific Oligonucleotide Probe (SSOP), etc. However, most of these methods have some shortcomings, such as high cost, low accuracy, or complicated procedures, etc. A common problem faced by these techniques is that neither is capable of high-throughput/large-scale genetic polymorphism analysis. In order to deal with the need for high-throughput analysis for genetic polymorphisms, new techniques are being developed by international efforts. For example, Matrix-Assisted Laser Desorption/Ionization Time-of-Flight Mass Spectrometry (MALDI-TOF MS), Ligase Detection Reaction (LDR), Single-Base Chain Extension (SBE), Bead Array, Universal Array, and High-Density Microarray, etc.

Among the above-mentioned techniques, Allele-Specific PCR (ASPCR) is an easy-to-practice method for polymorphism analysis. It was established by Newton et al. in 1989 (Newton, C. R., et al., *Nucleic Acid Res.* (1989) 17:2503-2516). Developed based on the PCR technique, ASPCR is also known as Amplification Refractory Mutation System (ARMS) or PCR-Sequence Specific Primer (PCR-SSP), etc. In order to analyze known mutations or polymorphisms in genetic sequences, ASPCR uses DNA polymerases without the 3'-5' exonuclease activity so that if the 3' end of a primer does not match the template, the primer can not be elongated and the PCR reaction is blocked. The ASPCR method is easy to practice but low-throughput, and is especially laborious when determining multiple polymorphisms simultaneously. In order to increase throughput, researchers have developed multiple strategies. Utilizing the theory of multiplex PCR, Robert et al. performed amplification of multiple polymorphic loci in which two separate PCR reactions were performed using primers specific for the wild-type and mutant alleles. See Ferrie, R. M., et al., *Am. J. Hum. Genet.* (1992) 51:251-262. PCR products are separated by electrophoresis in two lanes, one for wild-type and one for mutant, while different target loci are distinguished by the size of the PCR products. Gómez-Llorente et al. combined single reaction-multiplex PCR with capillary electrophoresis (Gómez-Llorente, M. A., et al., *Early Hum. Dev.* (2001) 65:S161-S164). Different target loci are distinguished by the size of PCR products while wild-type and mutant alleles are distinguished by labeling allele-specific primers with distinctly colored fluorescent dyes. Boniotto et al. combined single-reaction-multiplex PCR with melting temperature analysis to achieve multiplex polymorphism analysis (Boniotto, M., et al., *J Immunol. Methods* (2005) 304:184-188). They added GC tails to allele-specific primers in order to distinguish the $T_m$ values of the two alleles and used SYBR Green I for quantitative fluorescent analysis. Eaker et al. combined ARMS with DNA Chip analysis by following multiplex ARMS amplification with hybridizing the labeled PCR products to DNA Chip with allele-specific oligonucleotides in order to discriminate polymorphisms (Eaker, S., et al., *Biosensors Bioelectronics* (2005) 21:933-939).

Universal array is a high-throughput technique for sequence analysis which was first developed by Barany et al. (U.S. Pat. No. 6,506,594). It combines the LDR with microarray in order to detect low abundance genetic point-mutations with high sensitivity. The 3'-end of the LDR common probe is labeled with fluorescent dye, while the 5'-ends of the allele-specific probes are linked to distinct cZip-code sequences. The cZip-code sequences are artificially designed and subject to critical filtering so that they are complementary to the Zip-code sequences on the universal array. Each combination of cZip-code and Zip-code corresponds to an allele of a mutation or single nucleotide polymorphism (SNP) in the target gene. The upstream and downstream probes are ligated by ligase when the allele-specific probe is complementary to the DNA target. The ligated products are used to hybridize with the universal array and sequence variation can be interpreted by analyzing the position of the Zip-code and the fluorescence signal intensity. This method has high sensitivity and is capable of accurate detection of 1% or less mutant SNP occurrence among wild-type sequences. When the cZip-code sequences are linked to other specific probes, the same array designed for one set of targets can be used for any target sequences, which makes the array universal. Combining universal array with liquid enzyme-catalyzed reaction greatly overcame the problem of low-specificity of allele-specific oligonucleotide arrays for the analysis of genetic polymorphism (or mutation). A similar method for determining the genotype of one or more individuals at a polymorphic locus employing amplification of a region of DNA using primers containing tags and hybridization of the products to one or more probes on a solid support was introduced by Affymetrix, Inc. (PCT Publication No. WO 01/29259).

There are about 20 million deaf patients who make up the largest handicap population in China. Approximately 50% of these cases are hereditary. Mutations in many different genes may cause hereditary hearing loss. The highly heterogeneous nature of this disorder led to genetic sequencing being the major clinical assay for deaf patients which is complicated to operate, low-throughput, and expensive. Thus there exists the need for a high-throughput and cost-effective method for genetic diagnosis to improve clinical management of the genetic information of hereditary deaf patients.

All references, publications, and patent applications disclosed herein are hereby incorporated by reference in their entirety.

BRIEF SUMMARY OF THE INVENTION

The invention provides a method for determining polymorphisms in a sample comprising the steps of: a) performing multiple PCR amplifications with 1) a sample genomic DNA as a template; 2) a group of primers comprising one or more allele-specific primers for a target gene, a universal primer and a common primer; and 3) a DNA polymerase without 3'-5' exonuclease activity; wherein each allele-specific primer comprises a unique tag sequence linked to the 5' end of a nucleotide sequence which is identical or complementary to a target gene sequence containing the polymorphic locus; the Tm difference between different tag sequences equals or is less than 5° C.; and the tag sequences have no cross-hybridization among themselves or with the group of primers, have low homology to the species of the sample genomic DNA, and no hair-pin structures; wherein the common primer comprises, from 5' to 3', a nucleotide sequence identical to the nucleotide sequence of the universal primer and a nucleotide sequence which is identical or complementary to a sequence on the sample genomic DNA, and wherein each said allele-specific primer and said common primer generate a DNA fragment containing the polymorphic locus from PCR amplifications; b) hybridizing the PCR products generated in step a) to a DNA array comprising tag probes, wherein each tag probe comprises one of said tag sequences in said allele specific primers, and each said tag probe is able to hybridize to the complementary sequence in the PCR products; and c) determining the polymorphic genotype based on the hybridization signal and the position of the tag probe hybridized with the PCR products on the array.

The invention also provides a microarray chip for genotyping of hereditary deafness comprising twenty two different tag probes immobilized on a surface of the chip, wherein each immobilized tag probe comprises a nucleotide sequence selected from SEQ ID NOS:1-22.

The invention also provides a kit for determining polymorphisms in a sample comprising: 1) a group of primers comprising one or more allele-specific primers for a target gene, a universal primer and a common primer; 2) a DNA polymerase without 3'-5' exonuclease activity; and 3) a microarray chip comprising nucleic acid molecules immobilized on a surface of the chip; wherein each allele-specific primer comprises a unique tag sequence linked to the 5' end of a nucleotide sequence which is identical or complementary to a target gene sequence containing the polymorphic locus; the Tm difference between different tag sequences equals or is less than 5° C.; and the tag sequences have no cross-hybridization among themselves or with the group of primers, have low homology to the species of the sample genomic DNA, and no hair-pin structures; wherein the common primer comprises, from 5' to 3', a nucleotide sequence identical to the nucleotide sequence of the universal primer and a nucleotide sequence which is identical or complementary to a sequence on the sample genomic DNA, and wherein each said allele-specific primer and said common primer generate a DNA fragment containing the polymorphic locus from PCR amplifications; and wherein said nucleic acid molecules immobilized on the surface of the chip comprise one of said tag sequences in allele-specific primers.

DETAILED DESCRIPTION OF THE INVENTION

Figure 1:
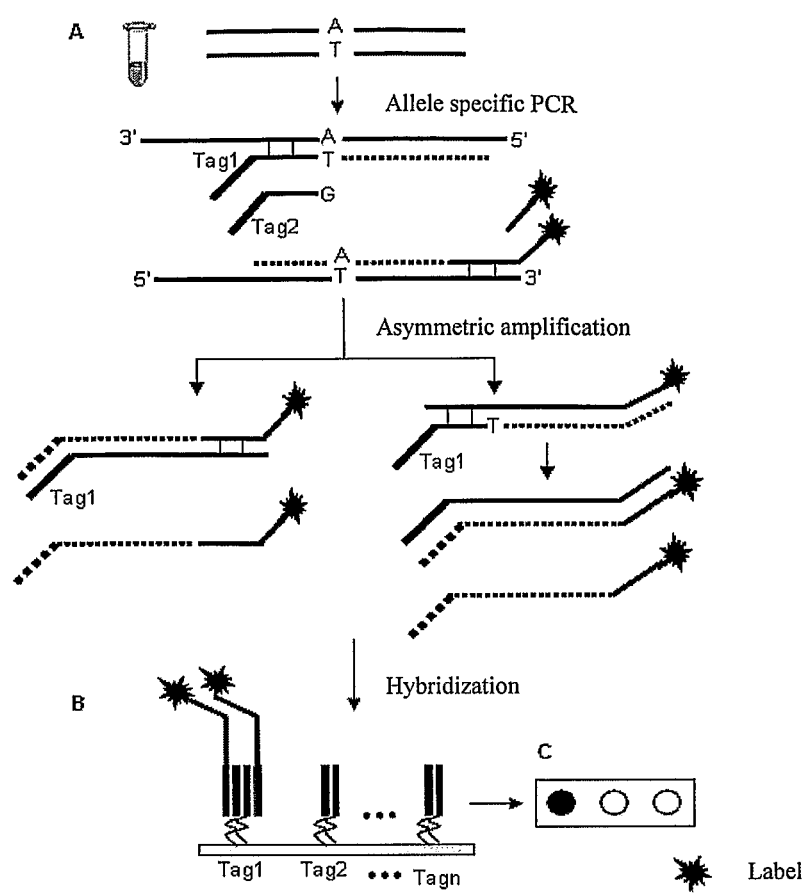
FIG. 1 illustrates a method of determining a polymorphism. (A) The first step shows PCR amplification of a region of a double stranded DNA sample containing a specific nucleotide at a polymorphic locus with allele-specific primer having tag 1 sequence, a fluorescent labeled universal primer, and a fluorescent labeled common primer. The second step shown is the asymmetrical PCR amplification. (B) The third step shown is the hybridization of the PCT products to a DNA chip on which probes comprising tag sequences are immobilized.

The present invention provides methods, microarrays, and kits for determining allele genotypes.

The invention provides a method for determining polymorphisms in a sample comprising the steps of: a) performing multiple PCR amplifications with 1) a sample genomic DNA as a template; 2) a group of primers comprising one or more allele-specific primers for a target gene, a universal primer and a common primer; and 3) a DNA polymerase without 3'-5' exonuclease activity; wherein each allele-specific primer comprises a unique tag sequence linked to the 5' end of a nucleotide sequence which is identical or complementary to a target gene sequence containing the polymorphic locus; the Tm difference between different tag sequences equals or is less than 5° C.; and the tag sequences have no cross-hybridization among themselves or with the group of primers, have low homology to the species of the sample genomic DNA, and no hair-pin structures; wherein the common primer comprises, from 5' to 3', a nucleotide sequence identical to the nucleotide sequence of the universal primer and a nucleotide sequence which is identical or complementary to a sequence on the sample genomic DNA, and wherein each said allele-specific primer and said common primer generate a DNA fragment containing the polymorphic locus from PCR amplifications; b) hybridizing the PCR products generated in step a) to a DNA array comprising tag probes, wherein each tag probe comprises one of said tag sequences in said allele specific primers, and each said tag probe is able to hybridize to the complementary sequence in the PCR products; and c) determining the polymorphic genotype based on the hybridization signal and the position of the tag probe hybridized with the PCR products on the array.

In some variations, the group of primers include a universal primer, and two allele-specific primers corresponding to a polymorphism locus and a common primer to amplify the target gene. Each allele specific primer comprises a unique tag sequence.

The tag sequences are designed to have the differences between the Tm value equal or less than 5° C. (i.e., all the tag sequences have similar Tm value). There is no detectable cross hybridization between different tag sequences and between the tags and the primers. The tag sequences do not have hairpin structures. The sequence homology between the tag and the species of the target gene to be detected is low. For example, identical or complementary continuous nucleotides between the two sequences are less than 10 nucleotides.

The DNA array used may be a universal array having many tag probes immobilized on a solid surface of the array. Each tag probe corresponds a tag sequence in an allele-specific primer, and comprises a sequence identical to the corresponding tag sequence. Each tag probe can hybridize with the complementary tag sequence produced by the PCR amplification.

Tag sequences may comprise 20-24 nucleotides. Tag sequences may be designed by methods of bioinformatics. Tag probes can also be derived from a biological species different from the species of the target gene. For example, if the species of the target gene is from human, the tag sequences can be derived from sequences of bacteria (such as tubercle bacillus). The tag sequence is single stranded oligonucleotide or peptide oligonucleotide.

One or more target genes may be detected using the methods described herein.

The 5' end of the common primer and the universal primer is labeled with a molecule that may be detected. The molecule includes, but is not limited to, a fluorescent molecule, a biotin, a chemiluminescence molecule, or a solid microparticle or nanoparticle.

The PCR amplification may be conducted in one tube, or in different tubes.

The allele of the target gene may be caused by single base substitution, insertion, or deletion, or by multiple-base substitution, insertion or deletion.

In some variations, the one or more allele-specific primers comprise two primers. One allele-specific primer comprises a sequence identical or complementary to a region of the wild-type target gene containing the polymorphic locus. The other allele-specific primer comprises a sequence identical or complementary to a region of the mutated target gene containing the polymorphic locus. The allele-specific primers may terminate at their 3' ends at the polymorphic locus.

To increase hybridization selectivity between the allele-specific primer and target DNA, an artificial mismatch near the 3'-end of the allele-specific primers may be introduced. The artificial mismatch can be a natural base (such as A, T, C, or G) or a nucleotide analog. See U.S. Pat. No. 5,780,233. There is a greater duplex thermal stability difference between a duplex containing two mismatches and a duplex containing one mismatch. This significantly increases the amplification product from the primer (having only the artificial mismatch) that matches with the target gene as compared to the amplification product from the primer that does not match with the target gene (i.e., having both artificial mismatch and natural mismatch). This increases the ability to discriminate between two target sequences having one nucleotide change and increases the detection sensitivity.

Multiplex asymmetric PCR may be used to obtain sufficient single strand DNA for hybridization. For example, methods described in WO 2006/021131 may be used. The concentration ratio of the common primer and the allele specific primer may be 10~25:1. The common primer may be linked at its 5' end to a sequence identical to the universal primer. During amplification, a labeled (such as a fluorescent labeled) universal primer may be used to increase the amount of the single strand amplified product. The Tm difference between the universal primer and the allele specific primer equals or is less than 5° C. The universal primer used does not have hairpin structures and does not form dimers with other primers. The sequence homology between the universal primer and the species of the target gene detected is low. For example, identical or complementary continuous nucleotides between the two sequences are less than 10 nucleotides.

In some variations, the allele is caused by gene mutation. Gene mutations may be a single base substitution, insertion, or deletion, or multiple-base substitution, insertion or deletion in the genome.

The method of the invention may be used to detect gene mutations related to the hereditary hearing loss. For example, mutations in GJB2 (cox26) (GenBank Accession Number (NM_004004.4), GJB3 (cox31) (GenBank Accession Number NM_024009.2), SLC26A4 (PDS) (GenBank Accession Number NM_000441.1), and 12S rRNA (MTRNR1) gene (GenBank Accession Number NC_001807.4).

The primers used may include any or all of eight allele-specific primers and one common primer for detecting mutations of 167delT, 176-191del16 (176del16), 235delC and 299-300delAT (299delAT) in the GJB2 (cox26) gene, two allele specific primers and one common primer for the 35delG in GJB2 (cox26) gene, four allele specific primers and one common primer for the 538 C>T and 547 G>A in GJB3 (cox31) gene, two allele specific primers and one common primer for the 707 T>C in the SLC26A4 (PDS) gene, two allele specific primers and one common primer for the 1555A>G in the MTRNR1 (12S rRNA) gene, two allele specific primers and one common primer for the 2168 A>G in the SLC26A4 (PDS), and two allele specific primers and one common primer for the IVS7-2 A>G in SLC26A4 (PDS).

The two allele-specific primers for detection of 35delG in GJB2 (cox26) may be linked at the 5' end to Tag 1 sequence (SEQ ID NO:1) and Tag 2 sequence (SEQ ID NO:2), respectively, as shown in Table 1.

The two allele-specific primers for detection of 167delT in GJB2 (cox26) may be linked at the 5' end to Tag 3 sequence (SEQ ID NO:3) and Tag 4 sequence (SEQ ID NO:4), respectively, as shown in Table 1.

The two allele-specific primers for detection of 176-191del16 in GJB2 (cox26) may be linked at the 5' end to Tag 5 sequence (SEQ ID NO:5) and Tag 6 sequence (SEQ ID NO:6), respectively, as shown in Table 1.

The two allele-specific primers for detection of 235delC in GJB2 (cox26) may be linked at the 5' end to Tag 7 sequence (SEQ ID NO:7) and Tag 8 sequence (SEQ ID NO:8), respectively, as shown in Table 1.

The two allele-specific primers for detection of 299-300delAT in GJB2 (cox26) may be linked at the 5' end to Tag 9 sequence (SEQ ID NO:9) and Tag 10 sequence (SEQ ID NO:10), respectively, as shown in Table 1.

The two allele-specific primers for detection of 538 C>T in the GJB3 (cox31) may be linked at the 5' end to Tag 11 sequence (SEQ ID NO:11) and Tag 12 sequence (SEQ ID NO:12), respectively, as shown in Table 1.

The two allele-specific primers for detection of 547 G>A in the GJB3 (cox31) may be linked at the 5' end to Tag 13 sequence (SEQ ID NO:13) and Tag 14 sequence (SEQ ID NO:14), respectively, as shown in Table 1.

The two allele-specific primers for detection of 707 T>C in SLC26A4 (PDS) may be linked at the 5' end to Tag 15 sequence (SEQ ID NO:15) and Tag 16 sequence (SEQ ID NO:16), respectively, as shown in Table 1.

The two allele-specific primers for detection of 1555A>G in MTRNR1 may be linked at the 5' end to Tag 17 sequence (SEQ ID NO:17) and Tag 18 sequence (SEQ ID NO:18), respectively, as shown in Table 1.

The two allele-specific primers for detection of 2168A>G in SLC26A4 (PDS) may be linked at the 5' end to Tag 19 sequence (SEQ ID NO:19) and Tag 20 sequence (SEQ ID NO:20), respectively, as shown in Table 1.

The two allele-specific primers for detection of IVS7-2 A>G in SLC26A4 (PDS) may be linked at the 5' end to Tag 21 sequence (SEQ ID NO:21) and Tag 22 sequence (SEQ ID NO:22), respectively, as shown in Table 1.

In some variations, the microarray comprises twenty two tag probes, and each tag probe on the universal array comprises a nucleotide sequence of any one of the tag sequences shown in Table 1. In some variations, the tag probes are 5'-amino-modified. In some variations, the tag probes comprise a 15-nucleotide poly T oligonucleotide linked to the 5' end of the tag sequence.

The methods of the invention can be combined with micro total analysis system to form automatic detection instruments.

The invention provides microarrays for genotype detection of hereditary hearing loss. In some variations, the microarray comprises twenty two different tag probes immobilized on a surface of the microarray, wherein one tag probe comprises the nucleotide sequence of SEQ ID NO:1, one tag probe comprises the nucleotide sequence of SEQ ID NO:2, one tag probe comprises the nucleotide sequence of SEQ ID NO:3, one tab probe comprises the nucleotide sequence of SEQ ID NO:4, one tag probe comprises the nucleotide sequence of SEQ ID NO:5, one tag probe comprises the nucleotide sequence of SEQ ID NO:6, one tag probe comprises the nucleotide sequence of SEQ ID NO:7, one tag probe comprises the nucleotide sequence of SEQ ID NO:8, one tag probe comprises the nucleotide sequence of SEQ ID NO:9, one tag probe comprises the nucleotide sequence of SEQ ID NO:10, one tag probe comprises the nucleotide sequence of SEQ ID NO:11, one tag probe comprises the nucleotide sequence of SEQ ID NO:12, one tag probe comprises the nucleotide sequence of SEQ ID NO:13, one tag probe comprises the nucleotide sequence of SEQ ID NO:14, one tag probe comprises the nucleotide sequence of SEQ ID NO:15, one tag probe comprises the nucleotide sequence of SEQ ID NO:16, one tag probe comprises the nucleotide sequence of SEQ ID NO:17, one tag probe comprises the nucleotide sequence of SEQ ID NO:18, one tag probe comprises the nucleotide sequence of SEQ ID NO:19, one tag probe comprises the nucleotide sequence of SEQ ID NO:20, one tag probe comprises the nucleotide sequence of SEQ ID NO:21, and one tag probe comprises the nucleotide sequence of SEQ ID NO:22. In some variations, the 5' end of the twenty two tag probes are amino modified. In some variations, the 5' end of the twenty two tag probes are linked to oligonucleotide $T_n$, wherein n is 5, 6, 7, 8, 9, 10, 11, 12, 13, 14, 15, 16, 17, 18, 19, or 20.

The invention also provides kits for genotype detection of hereditary hearing loss comprising a microarray described herein.

The invention also provides a kit for determining polymorphisms in a sample comprising: 1) a group of primers comprising one or more allele-specific primers for a target gene, a universal primer and a common primer; 2) a DNA polymerase without 3'-5' exonuclease activity; and 3) a microarray chip comprising nucleic acid molecules immobilized on a surface of the chip. Each allele-specific primer comprises a unique tag sequence linked to the 5' end of a nucleotide sequence which is identical or complementary to a target gene sequence containing the polymorphic locus. The Tm difference between different tag sequences equals or is less than 5° C.; and the tag sequences have no cross-hybridization among themselves or with the group of primers, have low homology to the species of the sample genomic DNA, and have no hair-pin structures. The common primer comprises, from 5' to 3', a nucleotide sequence identical to the nucleotide sequence of the universal primer and a nucleotide sequence which is identical or complementary to a sequence on the sample genomic DNA, and each said allele-specific primer and said common primer generate a DNA fragment containing the polymorphic locus from PCR amplifications. The nucleic acid molecules immobilized on the surface of the chip comprise one of said tag sequences in allele-specific primers. In some variations, the allele-specific primers, the common primers, and the universal primer shown in Table 1 are included in the kit.

FIG. 1 provides an example of a multiplex allele-specific PCR-based universal array (ASPUA) system. Multiplex allele-specific PCR is carried out (for example, using HOT-STARTAQ® DNA Polymerase), and then the PCR products are used to hybridize with capture probes on a universal array. Results are determined by the signal intensity and by the position of the tag probe bound on the array. For each polymorphic locus, two tagged allele-specific primers that differ at their 3'-terminal base and terminate at their 3' end at the polymorphic locus. The HOTSTARTAQ® DNA Polymerase used lacks a 3' to 5' exonuclease activity; thus, if a PCR primer has a mismatch with the template at its 3'-terminal base, the efficiency of amplification is greatly reduced. The common primer is linked at its 5' end a tail sequence, and a universal primer which has the same sequence as the tail sequence is also used to increase the amount of the single strand DNA amplified. In the ASPUA assay, the universal array serves as a decoding tool to display the previous amplification results. The probes comprising sequences identical to their corresponding tag sequences in allele-specific primers are immobilized on a solid surface of the universal array. The result can be interrogated by the position of the tag probe and the fluorescence signal intensity.

The multiplex PCR in this invention is different from the common multiplex PCR. Firstly, there are two allele-specific primers which have different bases at the 3'-terminal. One primer is matched with the wildtype allele of the mutation or single nucleotide polymorphism (SNP), while the other primer is matched with the mutant allele. The allele-specific primers terminate at their 3' end at the mutation or polymorphic locus. The two allele-specific primers are used for comparison. This design increases the specificity and accuracy. Secondly, the tag sequence at the 5' end of the primer is used as the code for the polymorphic locus detected. In addition, artificial mismatches may be introduced to enhance the specificity of the primer. A universal primer sequence is linked to the 5' end of the common primer to increase the sensitivity. A fluorescent labeled universal primer is also added into the PCR reaction system after two rounds of PCR reactions. The fluorescent labeled universal primer is bound to the PCR products containing the complementary sequence, and amplification is continued to increase the amount of single stranded DNA to increase hybridization signal.

The universal array in this invention is different from the common microarray. For common microarray, the probes on the array are allele specific oligonucleotides. Different target gene panel need different format of microarray. The universal array in this invention have immobilized tag probes which are specifically designed. Such tag probes are not allele specific oligonucleotides. The tag sequences can be used as codes for different mutation of different genes or different species. One format of universal array can be used for detection of any genotypes. So such array is universal. The process of detection is a kind of de-coding step. Such array is simple and cost-effective which is different from the common microarray.

The methods of the invention are cost-effective, easily-used, and are not time-consuming. The methods can easy be automated and used for mutation detection in clinical genetic diagnostics, pharmacogenomics, and forensic identification.

As used herein, the singular forms "a," "or," and "the" include plural referents unless the context clearly dictates otherwise.

It is understood that aspect and variations of the invention described herein include "consisting" and/or "consisting essentially of" aspects and variations.

EXAMPLES

The following examples are offered to illustrate but not to limit the invention. The experiments listed below are all routine experiments except where otherwise noted.

Example 1

Analysis of Patient Samples with Known Mutant Alleles in Hereditary Deaf Genes Using the Universal Array and Method of the Current Invention 1. Sources of Clinical Sample and DNA Extraction Patient samples with known mutant alleles in hereditary deaf genes were provided by the Department of Ear Nose and Throat of the Chinese PLA General Hospital. Genomic DNA was isolated from whole blood samples using the Wizard® Genomic DNA Purification Kit (Promega, Madison, Wis., USA).

2. Synthesis of Primers for Multiplex PCR and Probes for Universal Array

Multiplex PCR primers and probes used for analyzing a total of 11 mutation loci in 4 target genes listed in Table 1 are the following:

(1) Primers

Sequences of all primers for the multiplex PCR are shown in Table 1.

In column Mutation Type "del" represents a deletion mutation, e.g., 35delG means a deletion of G at position 35 of the GJB2 gene with GenBank Accession Number of NM_004004.4; ">" represents a substitution mutation, e.g., 538C>T means a substitution of C by T at position 583 of the GJB3 gene with GenBank Accession Number of NM_024009.2.

Primer Names with a "WT" suffix represents an allele-specific primer capable of specifically amplifying the wild-type allele including the polymorphic locus. Primer Names with a "MU" suffix represents an allele-specific primer capable of specifically amplifying the mutant allele including the polymorphic locus. Primer Names with a "C" suffix represents a common primer capable of amplifying both the wild-type allele and the mutant allele of the target genetic fragment including the polymorphic locus. For each polymorphic locus the two allele-specific primers respectively pair with the common primer, e.g., 35delG-WT pairs with 35delG-C, 35delG-MU pairs with 35delG-C.

Tag1-Tag22 in the Primer Sequences column have the nucleotide sequences of SEQ ID NO:1-22 in the Tag Sequence column, respectively. "UP" in the common primer sequences represents the sequence of the universal primer. The sequence of the universal primer is "GCACGCTAT-CACGTTAGAC" (SEQ ID NO:52). The 5'-termini of the common primers were modified by the fluorescent label TAMRA.

In order to improve assay specificity, artificial mismatches (underlined) were introduced into some of the allele-specific primers.

The 3'-end nucleotides (bold) of the allele-specific primers 538C>T-WT, 547G>A-WT, 707T>C-WT, 2168A>G-WT are the same as the nucleotides of the wild-type allele at the target gene polymorphic loci. The 3'-end nucleotides (bold) of the allele-specific primers 538C>T-MU, 547G>A-MU, 707T>C-MU, and 2168A>G-MU are the same as the nucleotides of the mutant allele at the target gene polymorphic loci. The 3'-end nucleotides (bold) of the allele-specific primers IVS7-2A>G-WT and 1555A>G-WT are complementary to the nucleotides of the wild-type allele at the target gene polymorphic loci. The 3'-end nucleotides (bold) of the allele-specific primers 1555A>G-MU and IVS7-2A>G-MU are complementary to the nucleotides of the mutant allele at the target gene polymorphic loci.

(2) Probes

The universal array is a matrix made up of 22 Tag probes, capable of hybridizing to the multiplex PCR products, positive quality control for sample spotting (QC), negative quality control for sample spotting (BC), positive quality control for hybridization (PC), and negative quality control for hybridization (NC). QC is an oligonucleotide probe labeled with Hex at one end and modified by an amino group at the other end to monitor the efficiency of sample spotting and fixing on the array. Its sequence is $NH_2$-TTTTTTTTTTTTTTA-GAGTGCTTGGTGCCATAAC-HEX (SEQ ID NO:53). BC is 50% DMSO and spotted after QC for quality control of contamination by residual sample during sample spotting. NC is an oligonucleotide probe modified by an amino group which is incapable of hybridizing to any sequence being analyzed in the hybridization solution for quality control of nonspecific hybridization. Its sequence is $NH_2$-TTTTTTTTTTTTTTTGCAACCACCACCGGAGG (SEQ ID NO:54). PC is an oligonucleotide probe modified by an amino group which is capable of hybridizing to the fluorescently labeled complimentary sequence (c-PC) added to the hybridization solution for quality control of specific hybridization. Its sequence is $NH_2$-TTTTTTTTTTTTTTTGG-TATCGCGACCGCATCCCAATCT (SEQ ID NO:55).

The tag probes on the universal array are designed according to the format: $NH_2$-TTTTTTTTTTTTTTT-TagX (SEQ ID NOS:56-77) where X is a natural number between 1 and 22. For example, the sequence structure of Tag 1 probe is $NH_2$-TTTTTTTTTTTTTTT-Tag 1 (SEQ ID NO:56), the format of Tag 22 probe is $NH_2$-TTTTTTTTTTTTTTT-Tag 22 (SEQ ID NO:77), i.e., the Tag probes (SEQ ID NOS:56-77) have a 5'-amino group modification, followed by poly T15, followed by Tag1 to Tag 22 with the sequences of nucleotide sequences 1 to 22 listed in Table 1, respectively. The nucleotide sequences of Tag1 to Tag22 have the identical sequence to the corresponding Tag1 to Tag22 of the primer sequences, respectively.

All the primers and probes were synthesized and purified by Invitrogen Co., Shanghai, China.

TABLE 1

Mutations, ASUPA Primers and Tag Sequences.

| Gene/GenBank No. | Mutation Type | Primer Name | Primer Sequence (5'→3') | Tag Sequence (5'→3') |
|---|---|---|---|---|
| GJB2 NM_004004.4 | 35delG | 35delG-WT | Tag1-TGTTTGTTCACACCCCGCAG (SEQ ID NO: 23) | GTTACTGCTACGCGTGCT ACGT (SEQ ID NO: 1) |
| | | 35delG-MU | Tag2-TGTTTGTTCACACCCGCAG (SEQ ID NO: 24) | CATGAGCAAGCTGTCTAA GGCG (SEQ ID NO: 2) |
| | | 35delG-C | TAMRA-UP-GCATGCTTGCTTACCCAGAC (SEQ ID NO: 25) | |
| | 167delT | 167delT-WT | Tag3-CGACTTTGTCTGCAACACCCTG (SEQ ID NO: 26) | CGACGAGCTGCCGCGCAA GAT (SEQ ID NO: 3) |
| | | 167delT-MU | Tag4-ACTTTGTCTGCAACACCCG (SEQ ID NO: 27) | TATCGCGACCGCATCCAA TCT (SEQ ID NO: 4) |
| | 176del16 | 176del16-WT | Tag5-CCAGGCTGCAAGAACGTGTG (SEQ ID NO: 28) | GCTCGAAGAGGGCTACAG ATC (SEQ ID NO: 5) |
| | | 176del16-MU | Tag6-ACCCTGCAGCCAGCTACG (SEQ ID NO: 29) | TTCCCGTCCGTCATCGCTC AAG (SEQ ID NO: 6) |
| | 235delC | 235delC-WT | Tag7-ATCCGGCTATGGGCCCTG (SEQ ID NO: 30) | GATCGGCGGTGAAGCGAA AGG (SEQ ID NO: 7) |
| | | 235delC-MU | Tag8-ATCCGGCTATGGGCCTG (SEQ ID NO: 31) | GATGGTGATCTCGCGCGT GCG (SEQ ID NO: 8) |
| | 299delAT | 299delAT-WT | Tag9-TGGCCTACCGGAGACATGA (SEQ ID NO: 32) | TGTGCGCCCGAGTTC GGTATC (SEQ ID NO: 9) |
| | | 299delAT-MU | Tag10-CGTGGCCTACCGGAGACGA (SEQ ID NO: 33) | TTGATCCCATCGAAGGAC GATG (SEQ ID NO: 10) |
| | | GJB2-C | TAMRA-UP-GAGCCTTCGATGCGGACC (SEQ ID NO: 34) | |
| GJB3 NM_024009.2 | 538C>T | 538C>T-WT | Tag11-GTGGACTGCTACATTGGCC (SEQ ID NO: 35) | TGATGCGTCTGGGACGTG CCTG (SEQ ID NO: 11) |
| | | 538C>T-MU | Tag12-GTGGACTGCTACATTGGCT (SEQ ID NO: 36) | CAGAGCATCAACGACGCA GGA (SEQ ID NO: 12) |
| | 547G>A | 547G>A-WT | Tag13-ACATTGCCAGACCTACCG (SEQ ID NO: 37) | ACGATCAACGCGGAGACA CAG (SEQ ID NO: 13) |
| | | 547G>A-MU | Tag14-TACATTGCCAGACCTACCA (SEQ ID NO: 38) | ACGAGACACGCAACGAG ACAG (SEQ ID NO: 14) |
| | | GJB3-C | TAMPA-UP-TCGAGGCTTGTCCTTGTGC (SEQ ID NO: 39) | |
| SLC26A4 NM_000441.1 | 707T>C | 707T>C-WT | Tag15-CAAGTGCTGGTCTCACAGCT (SEQ ID NO: 40) | TTGAAAGCCTACACGCGA GCG (SEQ ID NO: 15) |
| | | 707T>C-MU | Tag16-AAGTGCTGGTCTCACAGCC (SEQ ID NO: 41) | CAAGCAGAGCTATGGTTC GCTG (SEQ ID NO: 16) |
| | | 707T>C-C | TAMRA-UP-GAGGTCTCACGTCTCAAACTC C (SEQ ID NO: 42) | |
| | 2168A>G | 2168A>G-WT | Tag19-GACACATTCTTTTTGTCGGTCCA (SEQ ID NO: 43) | GTTAGGGTCGGCCAAACT CTCC (SEQ ID NO: 19) |
| | | 2168A>G-MU | Tag20-ACATTCTTTTTGACGGTCCG (SEQ ID NO: 44) | GACAAAGGTCTGCCCAGC ACCA (SEQ ID NO: 20) |
| | | 2168A>G-C | TAMRA-UP-CAAGGTTTTCCAGATTGCTGAG (SEQ ID NO: 45) | |

TABLE 1-continued

Mutations, ASUPA Primers and Tag Sequences.

| Gene/ GenBank No. | Mutation Type | Primer Name | Primer Sequence (5'→3') | Tag Sequence (5'→3') |
|---|---|---|---|---|
| | IVS7-2A>G | IVS7-2A>G-WT | Tag21-AATGGCAGTAGCAATTATCGACT (SEQ ID NO: 46) | TGCAACACGCTAGGATCT CCTC (SEQ ID NO: 21) |
| | | IVS7-2A>G-MU | Tag22-TGGCAGTAGCAATTATCGTCC (SEQ ID NO: 47) | TGCACTTCTCGGTAGGCA GCGA (SEQ ID NO: 22) |
| | | IVS7-2A>G-C | TAMRA-UP-CGTGTAGCAGCAGGAAGTAT (SEQ ID NO: 48) | |
| 12S rRNA NC_001807.4 | 1555A>G | 1555A>G-WT | Tag17-ACTTACCATGTTACGACTAGT (SEQ ID NO: 49) | GTCAGTATCGCGTTCGCTT ACG (SEQ ID NO: 17) |
| | | 1555A>G-MU | Tag18-CACTTACCATGTTACGACTTGC (SEQ ID NO: 50) | CCATACTCACGCAACTGT GCA (SEQ ID NO: 18) |
| | | 1555A>G-C | TAMRA-UP-CCCTGATGAAGGCTACAAAG (SEQ ID NO: 51) | |
| | | Universal Primer (UP) | TAMRA-GCACGCTATCACGTTAGAC (SEQ ID NO: 52) | |

(3) Fixation of Probes to Amino-Modified Glass Slides

Figure 3:
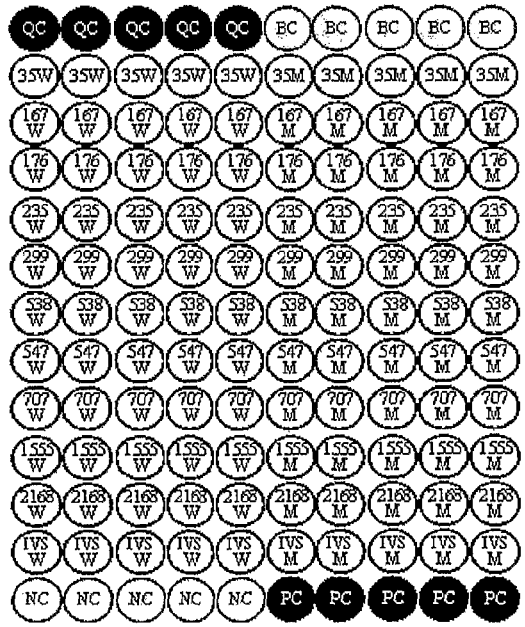
FIG. 3 shows the array format. QC and BC represent positive and negative controls of spotting efficiency, respectively. PC and NC represent oligonucleotides which served as positive and negative controls of hybridization, respectively.

All Tag probes were dissolved in 50% DMSO at a final concentration of 15 µM and printed as five replica spots on the glass slide. FIG. 3 illustrates the spot matrix on a universal array, showing that every spot in the matrix was replicated horizontally for 5 consecutive spots. The probes on the array include Tag1 to Tag10 for the analysis of the 35delG, 167delT, 176del16, 235delC, and 299delAT mutations in the GJB2 gene; Tag 11 to tag14 for the analysis of the 538C>T and 547G>A mutations in the GJB3 gene; Tag15, Tag16, Tag19, Tag20, Tag21 and Tag22 for the analysis of the 707T>C, 2168A>G and IVS7-2A>G mutations in the SLC26A4 gene; and Tag 17 and Tag18 for the analysis of the 1555A>G mutation in mitochondrial 12S rRNA. In FIG. 3, 35W represents the Tag1 probe, 35M represents the Tag2 probe, 167W represents the Tag3 probe, 167M represents the Tag4 probe, 176W represents the Tag5 probe, 176M represents the Tag6 probe, 235W represents the Tag7 probe, 235M represents the Tag8 probe, 299W represents the Tag9 probe, 299M represents the Tag10 probe, 538W represents the Tag11 probe, 538M represents the Tag12 probe, 547W represents the Tag13 probe, 547M represents the Tag14 probe, 707W represents the Tag15 probe, 707M represents the Tag16 probe, 1555W represents the Tag17 probe, 1555M represents the Tag18 probe, 2168W represents the Tag19 probe, 2168M represents the Tag20 probe, IVS7-2W represents the Tag21 probe, and IVS7-2M represents the Tag22 probe.

3. Multiplex Allele-Specific PCR

Universal primer (UP) was used in the multiplex PCR. The 5'-end of the common primers were linked to universal primers. Fluorescently labeled universal primers were added into the PCR system (with the same sequence as the universal primer at the end of the common primers). After the first two rounds of PCR reaction, complimentary sequences to the universal primer were produced. The complimentary sequences annealed to the fluorescently labeled universal primers and amplified, which increased the quantity of single-stranded DNA in the PCR products and enhanced hybridization signals.

Multiplex PCR was carried out using the genomic DNA from whole blood of patient samples as templates. Multiplex PCR was carried out in two tubes to avoid interactions between some primers. Primers 547G>A-WT, 547G>A-MU, GJB3-C, 2168A>G-WT, 2168A>G-MU, 2168A>G-C, IVS7-2 A>G-WT, IVS7-2 A>G-MU$_5$ and IVS7-2 A>G-C were amplified in one tube, and the remaining primers in Table 1 were amplified in another tube. Reaction volumes were 25 µl, and contained 0.2 mM dNTPs, 1×Qiagen PCR buffer, with addition of MgCl$_2$ to 2 mM, pH 8.7, 1 unit of HOTSTARTAQ® DNA Polymerase (Qiagen, Hilden, Germany) and 100 ng of genomic DNA, assay primers for each target locus, wherein the concentration of common primers was higher than allele-specific primers, and universal primers were added to the two tubes, respectively. The primer concentrations in a 25 µl reaction volume were as following: 35delG-WT 0.02 µM, 35delG-MU 0.02 µM, 35delG-C 0.4 µM, 167delT-WT 0.03 µM, 167delT-MU 0.03 µM, 176del16-WT 0.03 µM, 176del16-MU 0.03 µM, 235delC-WT 0.02 µM, 235delC-MU 0.02 µM, 299delAT-WT 0.02 µM, 299delAT-MU 0.03 µM, GJB2-C 0.6 µM, 538C>T-WT 0.02 µM, 538CT>T-MU 0.02 µM, 547G>A-WT 0.02 µM, 547G>A-MU 0.02 µM, GJB3-C 0.4 µM, 707T>C-WT 0.02 µM, 707T>C-MU 0.02 µM, 707T>C-C 0.3 µM, 2168A>G-WT 0.03 µM, 2168A>G-MU 0.03 µM, 2168A>G-C 0.4 µM, IVS7-2A>G-W 0.03 µM, IVS7-2A>G-MU 0.03 µM, IVS7-2A>G-C 0.4 µM, 1555A>G-WT 0.08 µM, 1555A>G-MU 0.08 µM, 1555A>G-C 0.2 µM, Universal Primer 1 µM.

Alternatively a 15 µl amplification system contained 0.2 mM dNTPs, 2 mM MgCl$_2$, 0.8 unit of HOTSTARTAQ® DNA Polymerase and 50 ng of genomic DNA, or 5 pg of plasmid DNA. The primer concentrations in a 15 µl reaction volume were as following: 35delG-WT 0.04 µM, 35delG-MU 0.05 µM, 35delG-C 0.4 µM, 167delT-WT 0.03 µM, 167delT-MU 0.03 µM, 176del16-WT 0.03 µM, 176del16-MU 0.03 µM, 235delC-WT 0.02 µM, 235delC-MU 0.02 µM, 299delAT-WT 0.02 µM, 299delAT-MU 0.03 µM, GJB2-C 0.6 µM, 538C>T-WT 0.02 µM, 538C>T-MU 0.02 µM, 547G>A-WT 0.02 µM, 547G>A-MU 0.01 µM, GJB3-C 0.3 µM, 707T>C-WT 0.01µM, 707T>C-MU 0.01 µM, 707T>C-C 0.3 µM, 2168A>G-WT 0.01 µM, 2168A>G-MU 0.01 µM, 2168A>G-C 0.4 µM, IVS7-2A>G-W 0.03 µM, IVS7-2A>G-MU 0.01 µM, IVS7-2A>G-C 0.4 µM, 1555A>G-WT 0.01µM, 1555A>G-MU 0.01 µM, 1555A>G-C 0.2 µM, UP 0.4 µM.

The amplification was performed in a PTC-225 Thermal Cycler (MJ Research, Watertown, Mass., USA). Amplification parameters were as follows: first 95° C. for 15 minutes; then 94° C. for 30 seconds, ramp at 0.5° C./second to 56° C., hold at 56° C. for 30 seconds; ramp at 0.2° C./second to 70° C., hold at 70° C. for 45 seconds, for 10 cycles; and then 90° C. for 30 seconds, ramp at 0.5° C./second to 56° C., hold at 56° C. for 30 seconds, ramp at 0.2° C./second to 70° C., hold at 70° C. for 45 seconds, for 22 cycles; finally 60° C. for 10 minutes; and 4° C. soak.

Amplification parameters were alternatively as follows: 95° C. for 15 minutes; then: 94° C. for 30 seconds, ramp 68 seconds to 55° C., hold for 30 seconds; ramp 50 seconds to 70° C., hold for 45 seconds for 10 cycles; then: 90° C. for 30 seconds, ramp 60 seconds to 55° C., hold for 30 seconds, ramp 50 seconds to 70° C., hold for 45 seconds for 20 cycles; followed by 60° C. for 10 minutes; and 4° C. soak.

4. Universal Array Hybridization

The products of both amplification reactions were combined. An aliquot of the mixture (10 µl) was suspended in 20 µl of hybridization buffer (6×SSC, 5×Denhardt's reagent, 25% formamide, 0.1% SDS, 5 nM c-PC (complimentary to PC probes on the array, labeled with TAMRA at the 5'-end)). After denaturing for 5 minutes at 98° C. and chilling on ice, the hybridization mixture was added to two neighboring matrices as duplicate experiments. The slide was incubated at 50° C. for 1 hour and washed 2 minutes each at 42° C. in two types of washing solutions (WSI: 0.3×SSC/0.1% SDS; WSII: 0.06×SSC). Finally, the slide was dried by centrifugation.

In order to validate the specificity of the universal array, artificially synthesized and fluorescently labeled Tag1 to Tag22 complimentary sequences (cTag1 to cTag22) were dissolved with hybridization buffer at 5 nM and hybridized to the array with the same conditions of hybridization and washing as described above.

5. Data Analysis

Figure 4:
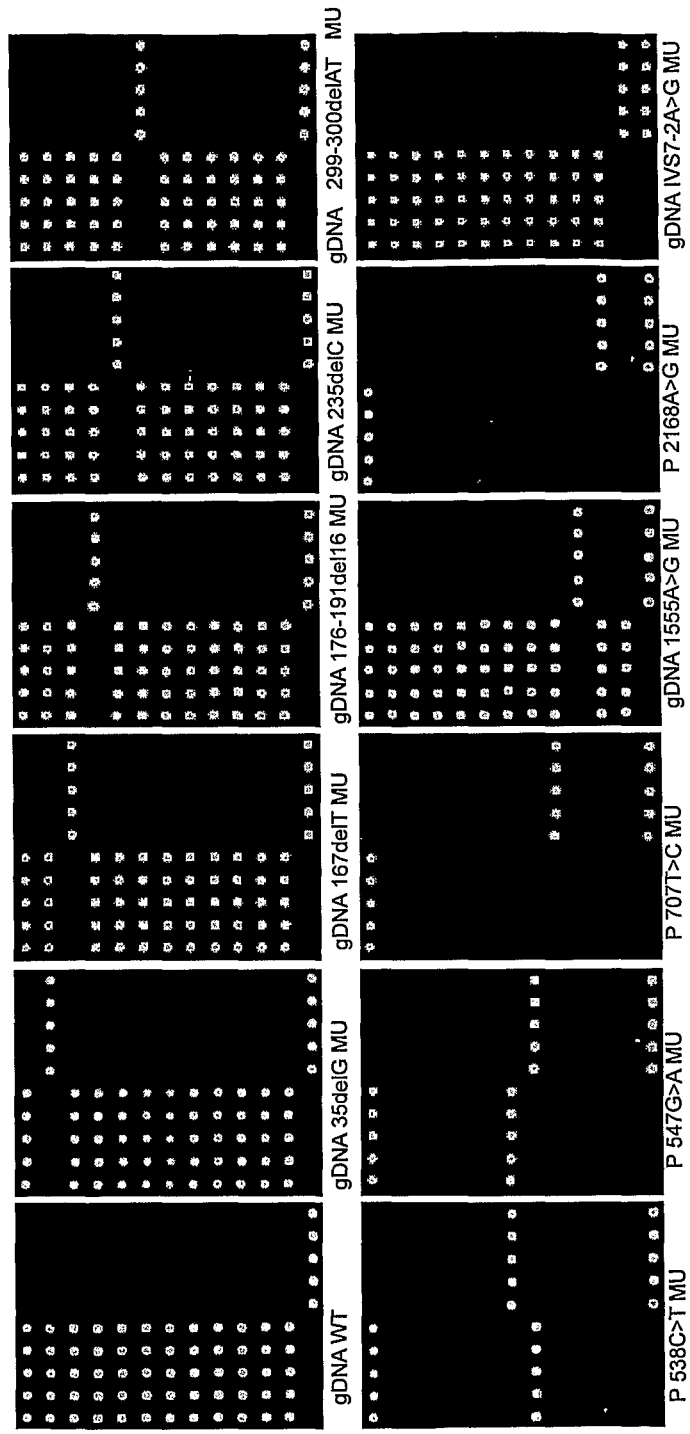
FIG. 4 shows the validation results of patient samples.

The dried slide was scanned with a ScanArray™ Express Microarray Scanner (PerkinElmer Life Sciences, Boston, Mass., USA). The scanned image is shown in FIG. 4. Laser power and photomultiplier tube (PMT) power were 90% and 70%, respectively. The signal intensities of the spots were quantified by GenePix Pro 4.0 (Axon Instruments, Foster City, Calif., USA). The absolute median signal intensity (AMSI) of each spot was calculated by subtracting the background signal intensity from the median signal intensity of the fluorescent signal, and a minimum value of 1000 was used as the cut-off for AMSI. To exclude false positive signals generated by primer dimers, AMSI for a target locus was required to be at least 10 times the value of that of negative PCR control (without template) AMSI for that locus. If these two criteria were met, the signal of a locus was considered to be positive. For universal array validation, the ratio value was used as a measure for the specificity of Tag probes. The criteria for specificity are: the ratio of each selected tag should be more than 10, while the AMSI was at least 1000.

$$\text{Ratio} = (AMSI)_{expected\ positive\ signal} / (AMSI)_{maximum\ negative\ signal}$$

Figure 2:
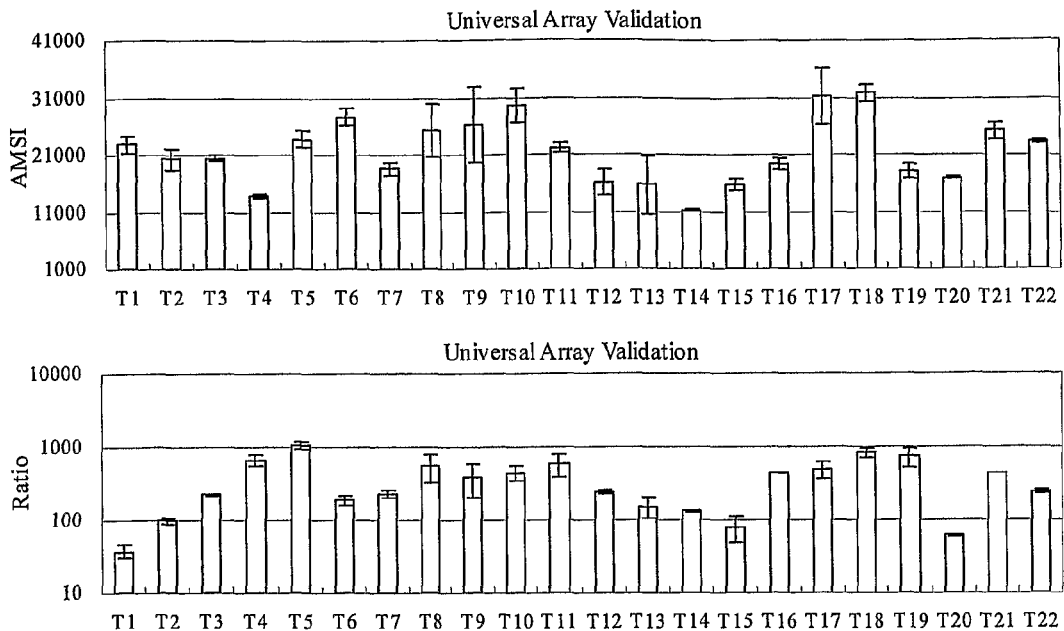
FIG. 2 shows the validation result using the universal array. "AMSI" refers to the absolute median signal intensity. T1 to T22 represents Tag 1 to Tag 22.

Results from the validation experiments of the universal array are shown in FIG. 2. T stands for Tag. For each one of Tag1 to Tag22 the AMSI was at least 1000 and the ratio was greater than 10. The results indicated that the universal array possessed high specificity.

FIG. 4 shows the detection results of the clinical samples from deaf patient using the universal array shown in FIG. 3. On the left of the array were probes of wild-type alleles; on the right were probes of mutant alleles. Each probe was printed horizontally as five replica spots. For the genomic DNA from a known wild-type sample, all the wild-type-specific probes on the left of the array showed positive signal while no hybridization signal was detected from mutation-specific probes on the right (as expected). Genomic DNA gDNA 235delC MU, gDNA 299delAT MU, gDNA 1555A>G MU and gDNA IVS7-2A>G MU were from patient samples with known hereditary deaf gene mutations 235delC MU, 299delAT MU, 1555A>G MU and IVS7-2A>G MU, respectively, representing four mutant situations. The corresponding mutation-specific probes in the hybridization maps gave the correct detection signals. Results shown in FIG. 4 demonstrate that detection results from all target loci were correct, and with high specificity.

Example 2

Magnetic Bead-Assisted Detection of ASPUA

In order to simplify the testing protocol and reduce the reliance on equipment by this method, we employed magnetic bead labeling so that assay results could be photographed with a CCD camera or viewed under low magnification microscope, which made the complicated genetic analysis easy and simple.

The 235delC and 299delAT mutations were chosen for this experiment. The fluorescent dyes on relevant primers and probes were replaced by biotin. The PCR parameters, hybridization and washing steps were conducted as described in Example 1. Streptavidin-coated MyOne™ Dynalbeads (Dynal Invitrogen, Oslo, Norway) were used to show hybridization results. Streptavidin-coated beads were first pretreated according to the protocol from the supplier, followed by the addition of magnetic bead buffer to the array block. After incubation for 10 minutes at room temperature, magnetic beads that were not specifically bound were removed by a magnet and the array dried by centrifugation. Finally, the image was viewed with light microscope and captured by a CCD camera.

Figure 5:
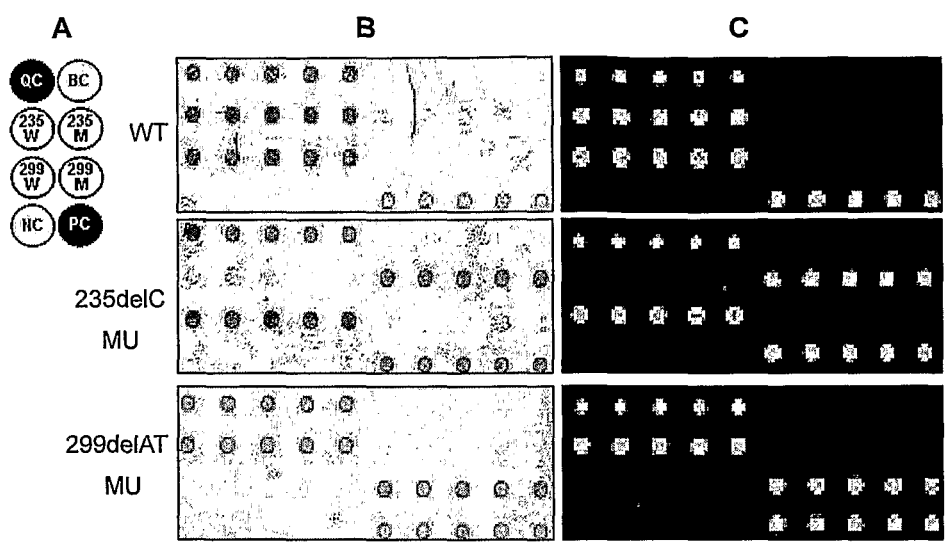
FIG. 5 shows layout of the universal chip (A), and the results of using magnetic beads (B) and fluorescent labels (C).

FIG. 5 shows the assay results. The matrix was in 4×10 format (see the matrix map in FIG. 5A), with every probe represented by 5 replica spots. The primers and probes used are shown in Table 1. The visible light-assisted detection results were clear, and in accordance to the fluorescent detection results shown on the right.

FIG. 5A illustrates the matrix position on the universal array. Each probe was printed as five horizontal replica spots. The probes included Tag7 to Tag10 which were specific for the 235delC and 299-300delAT mutant loci in the GJB2 gene. In FIG. 5A, 235W represents the Tag 7 probe, 235M represents the Tag 8 probe, 299W represents the Tag 9 probe, 299M represents the Tag 10 probe, QC is positive quality control for sample spotting, BC is negative quality control for sample spotting, PC is positive quality control for hybridization, and NC is negative quality control for hybridization. FIG. 5B is a result from a universal array hybridization detected with magnetic beads. FIG. 5C is a result detected with fluorescent signals. WT stands for known wild-type genomic DNA samples. 235delC MU and 299-300delAT MU were genomic DNA from patient samples with the 235delC and 299-300delAT mutant alleles.

What is claimed is:

1. A method for determining one or more polymorphisms in a sample comprising the steps of:
   (a) performing multiple PCR amplifications with 1) a sample genomic DNA as a template; 2) a group of primers comprising one or more allele-specific primers for a target gene, a universal primer and a common primer; and 3) a DNA polymerase without 3'-5' exonuclease activity,
   wherein each allele-specific primer comprises a unique tag sequence linked to the 5' end of a nucleotide sequence which is identical or complementary to a target gene sequence containing a polymorphic locus; the $T_m$ difference between different tag sequences equals or is less than 5° C.; and the tag sequences have no cross-hybridization among themselves or with the group of primers, have low homology to the species of the sample genomic DNA, and no hairpin structures; and
   wherein the common primer comprises, from 5' to 3', a nucleotide sequence identical to the nucleotide sequence of the universal primer and a nucleotide sequence which is identical or complementary to a sequence on the sample genomic DNA, wherein each said allele-specific primer and said common primer generate a DNA fragment containing the polymorphic locus from PCR amplifications, and wherein said universal primer increases the amount of single strand amplification product comprising a complementary sequence of the tag sequence of each allele-specific primer;
   b) hybridizing the PCR products generated in step a) to an array comprising tag probes, wherein each tag probe comprises one of said tag sequences in said allele-specific primers, and each said tag probe is able to hybridize to the complementary sequence in the PCR products; and c) determining the polymorphic genotype based on the hybridization signal and the position of the tag probe hybridized with the PCR products on the array, wherein the polymorphic locus is associated with hereditary deafness and is selected from the group consisting of: 35delG, 167delT, 176del16, 235delC, and 299delAT of GJB2; 538 C>T and 547 G>A of GJB3; 707 T>C, 2168 A>G, and IVS7-2 A>G of SLC26A4; and 1555 A>G of 12S rRNA, and wherein a primer comprising the tag sequence of SEQ ID NO:1 and a primer comprising the tag sequence of SEQ ID NO:2 are used to detect the 35delG mutation in the GJB2 gene; a primer comprising the tag sequence of SEQ ID NO:3 and a primer comprising the tag sequence of SEQ ID NO:4 are used to detect the 167delT mutation in the GJB2 gene; a primer comprising the tag sequence of SEQ ID NO:5 and a primer comprising the tag sequence of SEQ ID NO:6 are used to detect the 176del16 mutation in the GJB2 gene; a primer comprising the tag sequence of SEQ ID NO:7 and a primer comprising the tag sequence of SEQ ID NO:8 are used to detect the 235delC mutation in the GJB2 gene; a primer comprising the tag sequence of SEQ ID NO:9 and a primer comprising the tag sequence of SEQ ID NO:10 are used to detect the 299delAT mutation in the GJB2 gene; a primer comprising the tag sequence of SEQ ID NO:11 and a primer comprising the tag sequence of SEQ ID NO:12 are used to detect the 538 C>T mutation in the GJB3 gene; a primer comprising the tag sequence of SEQ ID NO:13 and a primer comprising the tag sequence of SEQ ID NO:14 are used to detect the 547 G>A mutation in the GJB3 gene; a primer comprising the tag sequence of SEQ ID NO:15 and a primer comprising the tag sequence of SEQ ID NO:16 are used to detect the 707 T>C mutation in the SLC26A4 gene; a primer comprising the tag sequence of SEQ ID NO:19 and a primer comprising the tag sequence of SEQ ID NO:20 are used to detect the 2168 A>G mutation in the SLC26A4 gene; a primer comprising the tag sequence of SEQ ID NO:21 and a primer comprising the tag sequence of SEQ ID NO:22 are used to detect the IVS7-2 A>G mutation in the SLC26A4 gene; and a primer comprising the tag sequence of SEQ ID NO:17 and a primer comprising the tag sequence of SEQ ID NO:18 are used to detect the 1555 A>G mutation in the 12S rRNA gene.

2. The method of claim 1, wherein the universal primer and the common primer are labeled with a detectable molecule.

3. The method of claim 1, wherein the PCR amplifications are conducted in one tube or in multiple tubes.

4. The method of claim 1, wherein said one or more allele-specific primers comprises two primers, wherein one primer comprises a nucleotide sequence which is identical or complementary to the sequence of the wildtype allele, and another primer comprises a nucleotide sequence which is identical or complementary to the sequence of the allelic variation.

5. The method of claim 4, wherein said two primers further comprise an artificial nucleotide mismatch, wherein the mismatch is a natural nucleotide or an analog.

6. The method of claim 1, wherein the $T_m$ difference between the universal primer and allele-specific primers equals or is less than 5° C., and wherein the universal primer does not form hairpin structures and dimers with other primers, and has low homology to the species of the sample genomic DNA and no cross-hybridization to said tag sequence.

7. The method of claim 1, wherein the array comprises the twenty-two different tag probes set forth in SEQ ID NOs:1-22.

8. The method of claim 1, wherein the array comprises at least four nucleotide sequences selected from SEQ ID NOs: 1-22.

9. The method of claim 2, wherein the detectable molecule is selected from the group consisting of a fluorescent molecule, a biotin, a chemiluminescence molecule, a microparticle, and a nanoparticle.

10. The method of claim 1, wherein the genotypes of polymorphisms in more than one target gene are determined.

\* \* \* \* \*